US010652990B2

(12) United States Patent
Butani et al.

(10) Patent No.: US 10,652,990 B2
(45) Date of Patent: May 12, 2020

(54) SYSTEM AND METHOD FOR VOICE CONTROL OF CABINET X-RAY SYSTEMS

(71) Applicant: KUB Technologies, Inc., Stratford, CT (US)

(72) Inventors: Vikram Butani, Stratford, CT (US); Yan Chen, Stratford, CT (US); Chester Lowe, Stratford, CT (US); Roberto Velasco, Stratford, CT (US); Edwin Divakaran Maria-Selvaraj, Stratford, CT (US); Vignesh Mandalapa-Bhoopathy, Stratford, CT (US); Timothy Ely, Stratford, CT (US)

(73) Assignee: KUB Technologies, Inc., Stratford, CT (US)

( * ) Notice: Subject to any disclaimer, the term of this patent is extended or adjusted under 35 U.S.C. 154(b) by 154 days.

(21) Appl. No.: 15/892,482

(22) Filed: Feb. 9, 2018

(65) Prior Publication Data

US 2018/0228010 A1    Aug. 9, 2018

Related U.S. Application Data

(60) Provisional application No. 62/456,707, filed on Feb. 9, 2017.

(51) Int. Cl.
*H05G 1/30* (2006.01)
*H05G 1/06* (2006.01)
*A61B 6/00* (2006.01)

(52) U.S. Cl.
CPC .............. *H05G 1/30* (2013.01); *A61B 6/00* (2013.01); *H05G 1/06* (2013.01)

(58) Field of Classification Search
CPC ... A61B 6/5247; A61B 8/0825; A61B 6/4417; A61B 8/4416; G01N 23/04; G01N 23/046
See application file for complete search history.

(56) References Cited

U.S. PATENT DOCUMENTS

| | | | |
|---|---|---|---|
| 2005/0111620 A1* | 5/2005 | Livermore | A61B 5/055 378/63 |
| 2007/0213617 A1* | 9/2007 | Berman | A61B 5/0091 600/473 |
| 2009/0110152 A1* | 4/2009 | Manzke | A61B 6/107 378/195 |
| 2015/0131773 A1 | 5/2015 | Lowe et al. | |
| 2015/0221091 A1* | 8/2015 | Sugiyama | A61B 6/502 382/131 |
| 2015/0320385 A1* | 11/2015 | Wright | A61B 5/0091 600/474 |

* cited by examiner

*Primary Examiner* — David P Porta
*Assistant Examiner* — Fani Boosalis
(74) *Attorney, Agent, or Firm* — Ziegler IP Law Group, LLC

(57) ABSTRACT

The present disclosure relates to a cabinet x-ray incorporating voice command operation for the production of organic and non-organic images. The computing device receives audio data and determines, based on the audio data, a voice-initiated action. In particular, the present disclosure relates to a system and method with corresponding apparatus for commanding the cabinet x-ray unit to attain, manipulate and optimize images.

20 Claims, 9 Drawing Sheets

Example of Embodiment integrated into Cabinet from Fig. 4

FRONT VIEW INTO CABINET
Door Open

Typical Example of an X-ray Cabinet System

View in Sample Chamber with Door Open with
X-ray source at position (14) Top Center Lateral View of X-Ray Source
Mounted to Swing Arm at position (14)

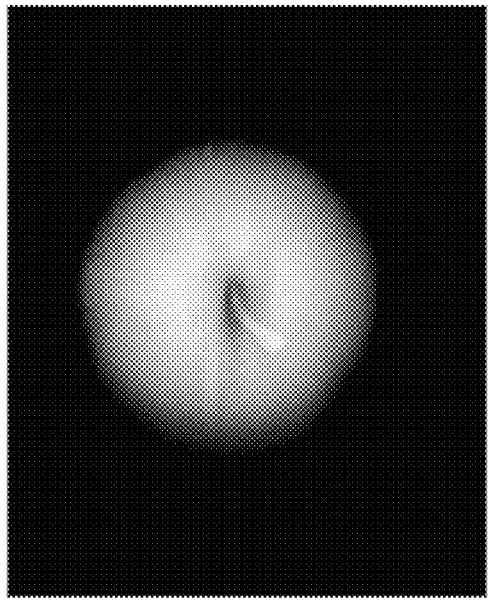
Fig. 7A -Top Slice – 59m
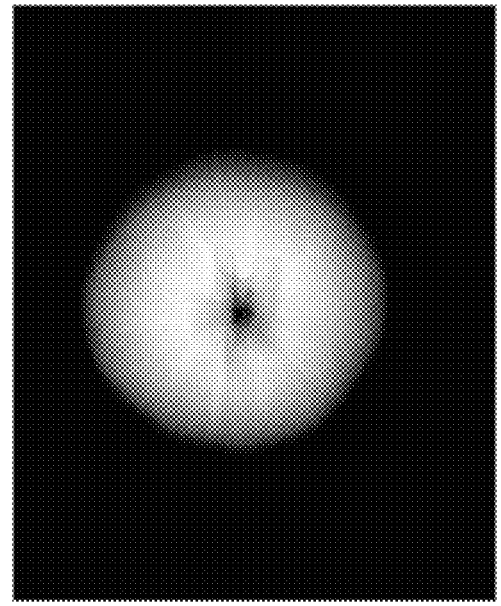
Fig. 7B - Bottom Slice – 13.5 mm
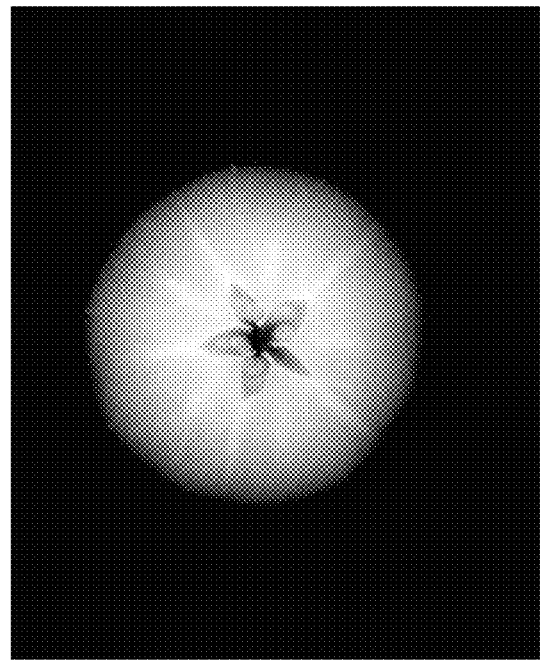
Fig. 7C - Middle Slice – 30.5 mm
Images of an Apple at multiple depth cuts
after tomosynthesis reconstruction from bottom up with the bottom at 0mm

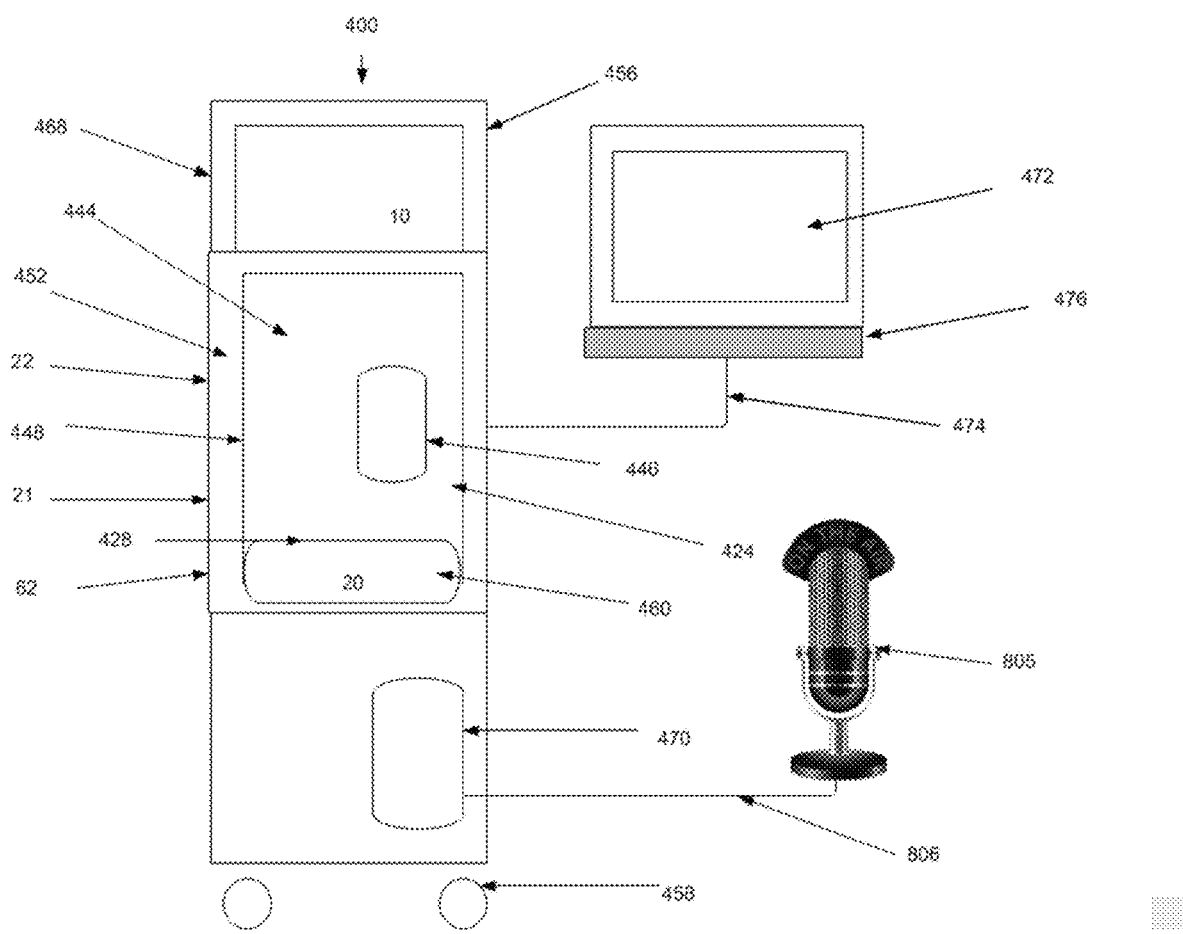
Fig. 8 – Example of Embodiment integrated into Cabinet from Fig. 4

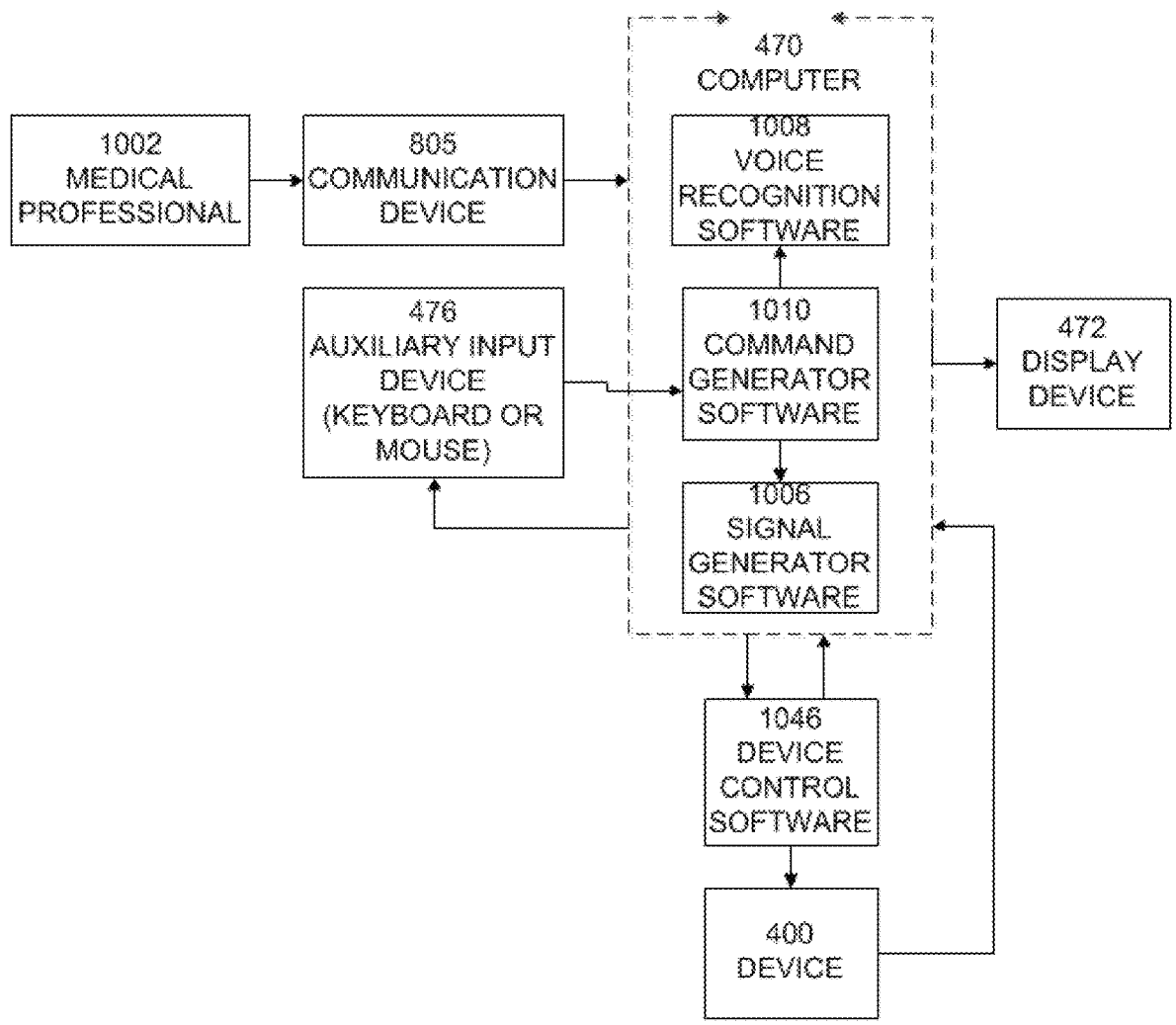
Fig. 9 – Basic Workflow

SYSTEM AND METHOD FOR VOICE CONTROL OF CABINET X-RAY SYSTEMS

CROSS-REFERENCE TO RELATED APPLICATIONS

This application claims priority to and the benefit of U.S. Provisional Patent Application Ser. No. 62/456,707 filed Feb. 9, 2017, the disclosure of which is incorporated herein by reference in its entirety.

BACKGROUND

Field of the Present Disclosure

Aspects of the present disclosure relate to the field of a cabinet x-ray incorporating a system and method for voice control of a cabinet x-ray system.

Background

Some computing devices (mobile phones, tablet computers, wearable computing devices, personal digital assistants, etc.) are "voice-activated" and can recognize voice commands based on audio input (a user's voice). For example, a computing device may receive voice input (audio data) with a microphone. The computing device may analyze the voice input using speech-recognition techniques/software to determine a command, i.e. "search", "play", "pause", etc. and then execute a voice-initiated action associated with the command. As such, a voice-activated computing device may provide users with the ability to operate some features of the computing device by speaking commands at the device.

It would be advantageous in breast procedure rooms and/or surgery suites to allow the medical professional to operate a cabinet x-ray unit that can be used to analyze the excised breast tissue or specimen utilizing voice commands. For example, certain medical instruments require the medical professional to use both hands and to stand next to the patient, sometimes in an awkward position throughout the entire procedure making it difficult for the medical professional to operate other equipment. At other times it is difficult for a pathology assistant to operate equipment while dissecting tissue specimens with both hands.

With a unit incorporating voice commands, the clinician can utilize the voice commands to expeditiously visualize the specimen excised from the patient without manual intervention with their gloved hands saving time for both the patient on the treatment table and the clinician.

Today, conventional breast specimen systems can gather a digital breast specimen radiogram separately. In these systems, the radiograms of a tissue or bone specimen are viewed separately for analysis.

Currently it is believed that there is not a system or method utilizing voice commands to control a cabinet x-ray system.

In general, this disclosure may enable a device (cabinet x-ray system) utilizing a computer to perform a voice-initiated action based on audio data/commands.

Breast cancer is the most common cancer among women other than skin cancer and is the second leading cause of cancer death in women after lung cancer. The American Cancer Society currently estimates that there are about 182,460 new cases of invasive breast cancer per year among women in the United States and 40,480 deaths per year from the disease. Prevention and early diagnosis of breast cancer are of foremost importance. Because early breast cancer does not produce symptoms, the American Cancer Society recommends an x-ray radiogram screening and a clinical breast examination every year for women over the age of 40. Recently, the American Cancer Society has additionally recommended an adjunctive breast MRI (magnetic resonance imaging) screening for women in certain higher-risk groups. Although the preferred embodiments described herein below are particularly applicable and advantageous for use in x-ray radiography, including, for example, x-ray mammography and x-ray tomosynthesis breast cancer screening procedures and protocols, they are also readily applicable for other breast imaging modalities such as breast specimen radiography and digital breast specimen tomosynthesis as well as x-ray radiography of other specimens including organic (i.e. living organisms) and non-organic (i.e. non-living organisms) specimens.

Lumps or abnormalities in the breast are often detected by physical examination, mammography, ultrasound, or other imaging studies. However, it is not always possible to tell from these imaging tests whether a growth is benign or cancerous.

Specimen radiography is considered one of the most cost-effective screening method for the detection of breast cancer in surgically removed breast tissue. However, the sensitivity of specimen radiography is often limited by the presence of overlapping dense fibroglandular tissue in the breast specimen. Dense parenchyma reduces the conspicuity of abnormalities and thus constitutes one of the main causes of missed breast cancer diagnosis. The advent of full-field digital detectors offers opportunities to develop advanced techniques for improved imaging of dense breasts, such as digital tomosynthesis.

A device receiving a voice command via a microphone, for example, and utilizing speech-recognition techniques/software to analyze the audio data may determine one or more voice commands for causing the device to perform voice-initiated actions allowing the medical professional to operate the cabinet x-ray equipment utilizing voice commands would free up personnel in the operating room as well as allow the medical professional to remain sterile and remain close to the patient.

Some embodiments may be utilized in to specimen radiography but they should not be limited only to specimen radiography and may be utilized for non-destructive testing, pathology as well as any radiographic analysis, organic and non-organic, requiring a cabinet x-ray system.

SUMMARY

The present disclosure relates to the field of a cabinet x-ray incorporating voice command operation for the production of organic and non-organic images. The computing device receives audio data and determines, based on the audio data, a voice-initiated action. In particular, the present disclosure relates to a system and method with corresponding apparatus for commanding the cabinet x-ray unit to attain and optimize images.

A preferred embodiment system would incorporate voice command into a cabinet x-ray unit allowing operation of the system freeing up the operator's hand/s.

In one embodiment, the aspects of the present disclosure are directed to a cabinet x-ray system incorporating a voice command unit. The system includes a cabinet x-ray system, a base unit including an image processor and a display and a microphone connected to the base unit. The base unit includes software or speech-recognition software; a system configured to receive analog signals relating to voice commands; a means to verify that speech command is recognized; a key word glossary; a processing unit that controls the speech recognition software and the analog-to-digital converter, causing the cabinet system to function; and an interface for enabling the analog/digital signal to be transferred from the microphone to the computer of the base unit. The cabinet x-ray system incorporating a voice command unit further includes performing, by the computing device, the voice-initiated action responsive to determining the voice-initiated action based on the audio data. The cabinet x-ray system incorporating a voice command unit wherein determining the voice-initiated action further includes generating by the computing device and based in part on the audio data, a transcription of the audio date: and determining, by the computing device and based at least in part on a comparison of at least one word from the transcription, or a phrase from the transcription to a preconfigured set of actions, the voice-initiated action which would be prefaced with a trigger word including "Mozart" or "Xpert". The cabinet x-ray system incorporating a voice command unit wherein determining the voice-initiated action further includes identifying, by the computing device, at least one verb in the transcription; and comparing, by the computing device, to at least one verb to one or more verbs from a set of verbs, each verb in the set of verbs corresponding to at least one action from a plurality of actions including the voice-initiated action including "zoom in" or "show K-view". The cabinet x-ray system incorporating a voice command unit wherein determining the voice-initiated action further includes determining, by the computing device and based in part on date from the computing device, a context; determined, by the computing device and based at least in part on the context, the voice-initiated action. The cabinet x-ray system incorporating a voice command unit wherein there is a proprietary set of commands and keywords. The cabinet x-ray system incorporating a voice command unit wherein the items examined may be organic and non-organic.

In another embodiment, the aspects of the present disclosure are directed to a computing device including at least with one processor and at least one software program operable by the at least one processor to output, for display, verification of the speech command; receive audio data; determining, based on the audio data, a voice-initiated action; and responsive to determining the voice-initiated action, output for display a change of the GUI/image to indicate that the voice-initiated command has been determined and recognized. The computing device may operate on MS Windows operating system. The computing device may utilize a proprietary speech recognition system/program.

In another embodiment, the aspects of the present disclosure are directed to a cabinet x-ray system including voice command. The system includes a cabinet defining an interior chamber, a display, a microphone and an x-ray system. The x-ray system includes an x-ray source, an x-ray detector, a specimen platform and a controller. The controller is configured to selectively energize the x-ray source to emit x-rays through the specimen to the x-ray detector, control the x-ray detector to collect a projection x-ray image of the specimen when the x-ray source is energized, selectively display an x-ray image on the display from the projection x-ray image, the x-ray image on the display including a first x-ray image having a first set of image parameters, receive a voice command from the microphone, the voice command including instructions to change the first x-ray image having the first set of image parameters to a second x-ray image having a second set of image parameters, the second set of image parameters being different from the first set of image parameters and change the x-ray image on the display different from the first x-ray image having the first set of image parameters to the second x-ray image having the second set of image parameters.

In another embodiment, the aspects of the present disclosure are directed to a cabinet x-ray system including voice command. The system includes a cabinet defining an interior chamber and an equipment enclosure, a display, a microphone and an x-ray system.

The x-ray system includes an x-ray source positioned in the interior chamber, an x-ray detector positioned in the interior chamber, a specimen platform positioned in the interior chamber and which is a protective cover of and in physical contact with the x-ray detector, a motion control mechanism positioned in the interior chamber and configured for moving the x-ray source to or along a plurality of positions within the interior chamber relative to the specimen disposed on the specimen platform; and a controller positioned in the equipment enclosure. The controller is configured to selectively energize the x-ray source to emit x-rays through the specimen to the x-ray detector at selected positions of the x-ray source relative to the specimen such that the isocenter of the emitted x-rays at the selected positions is located at a surface of the x-ray detector, control the x-ray detector to collect a projection x-ray images of the specimen when the x-ray source is energized at the selected positions, wherein one of the projection x-ray images is a two-dimensional x-ray image taken at standard imaging angle of approximately 0°, create a tomosynthetic x-ray image reconstructed from a collection of projection x-ray images, process the collection of the projection x-ray images in the controller into one or more reconstructed tomosynthetic x-ray images representing a volume of the specimen and relating to one or more image planes that are selectively the same or different from that of the two-dimensional x-ray image, selectively display an x-ray image on the display, the x-ray image on the display including at least one of the two-dimensional x-ray image and the one or more reconstructed tomosynthetic x-ray images and a first x-ray image having a first set of image parameters and receive a voice command from the microphone, the voice command including instructions to change the first x-ray image having the first set of image parameters to a second x-ray image having a second set of image parameters, the second set of image parameters being different from the first set of image parameters and change the x-ray image on the display from the first x-ray image having the first set of image parameters to the second x-ray image having the second set of image parameters.

In another embodiment, the aspects of the present disclosure are directed to a method for manipulating an x-ray image of a cabinet x-ray system using a voice command of a user. The cabinet x-ray system includes a cabinet defining an interior chamber, a display, a microphone and an x-ray system. The x-ray system includes an x-ray source, an x-ray detector, a specimen platform and a controller. The controller is configured to selectively energize the x-ray source to emit x-rays through the specimen to the x-ray detector, control the x-ray detector to collect a projection x-ray image of the specimen when the x-ray source is energized, selectively display an x-ray image on the display from the projection x-ray image, the x-ray image on the display including a first x-ray image having a first set of image parameters, receive a voice command from the microphone, the voice command including instructions to change the first x-ray image having the first set of image parameters to a second x-ray image having a second set of image parameters, the second set of image parameters being different from the first set of image parameters and change the x-ray image on the display different from the first x-ray image having the first set of image parameters to the second x-ray image having the second set of image parameters. The method includes controlling the x-ray detector to collect an x-ray image of the specimen when the x-ray source is energized, selectively displaying the first x-ray image having a first set of image parameters on the display, receiving a voice command from the user via the microphone, the voice command including instructions to change the first x-ray image having the first set of image parameters to the x-ray image having a second set of image parameters and changing the first x-ray image having the first set of image parameters on the display to the second x-ray image having the second set of image parameters.

BRIEF DESCRIPTION OF THE DRAWINGS

To further clarify the above and other advantages and features of the present disclosure, a more particular description of the disclosure will be rendered by reference to specific embodiments thereof that are illustrated in the appended drawings. It is appreciated that these drawings depict only typical embodiments and are therefore not to be considered limiting of its scope. Aspects of the present disclosure will be described and explained with additional specificity and detail through the use of the accompanying drawings in which:

FIGS. 7A, 7B and 7C—Displays the results of the imaging of an apple at multiple depth cuts after tomosynthesis reconstruction in a cabinet X-ray system incorporating aspects of the present disclosure.

FIG. 8 is an example of an X-ray Cabinet System incorporating aspects of the present disclosure including a microphone; and FIG. 9 is an exemplary workflow/flowchart of an aspect of the disclosed embodiments of the present disclosure.

DETAILED DESCRIPTION

Reference will now be made to figures wherein like structures will be provided with like reference designations. It is understood that the drawings are diagrammatic and schematic representations of exemplary embodiments and are not limiting nor are they necessarily drawn to scale.

FIGS. 1-9 depict various features of embodiments of the present disclosure, which embodiments are generally directed to a system that can utilize voice-initiated commands to perform functions.

The systems and methods of the present disclosure address the needs of the art by providing tomosynthesis apparatus and techniques for imaging breast specimens that overcome the shortfall of the data received from two-dimensional imaging systems. The aspects of the present disclosure enable the use of tomosynthesis to efficiently provide accurate three-dimensional imaging of a specimen in which overlapping images having differing attenuation characteristics by applying a three-dimensional reconstruction algorithm all in an x-ray cabinet.

As used herein, the term "computer," "computer system", or "processor" refers to any suitable device operable to accept input, process the input according to predefined rules, and produce output, including, for example, a server, workstation, personal computer, network computer, wireless telephone, personal digital assistant, one or more microprocessors within these or other devices, or any other suitable processing device with accessible memory.

The term "computer program" or "software" refers to any non-transitory machine readable instructions, program or library of routines capable of executing on a computer or computer system including computer readable program code. The "computer program" or "software" can stored on the storage device, such as, for example, a non-transitory computer readable medium, for example, a computer memory that can be associated with a computer, computer system or processor.

Digital breast specimen tomosynthesis as exhibited in U.S. Pat. No. 9,138,193 (2015/0131773), Lowe, et al., entitled "SPECIMEN RADIOGRAPHY WITH TOMOSYNTHESIS IN A CABINET," the disclosure of which is hereby incorporated by reference in its entirety in the present application, where aspects of the latter may help reduce, for example, the camouflaging effects of dense breast tissue and improve the sensitivity of specimen radiography for breast cancer detection in dense breasts.

Reference will now be made to figures wherein like structures will be provided with like reference designations. It is understood that the drawings are diagrammatic and schematic representations of exemplary embodiments of the present disclosure and are not limiting nor are they necessarily drawn to scale.

Specimen Tomography is a three-dimensional specimen imaging system. It involves acquiring images of a sample at multiple viewpoints, typically over an arc or linear path. The three-dimensional image is constructed by the reconstruction of the multiple image data set.

Figure 1:
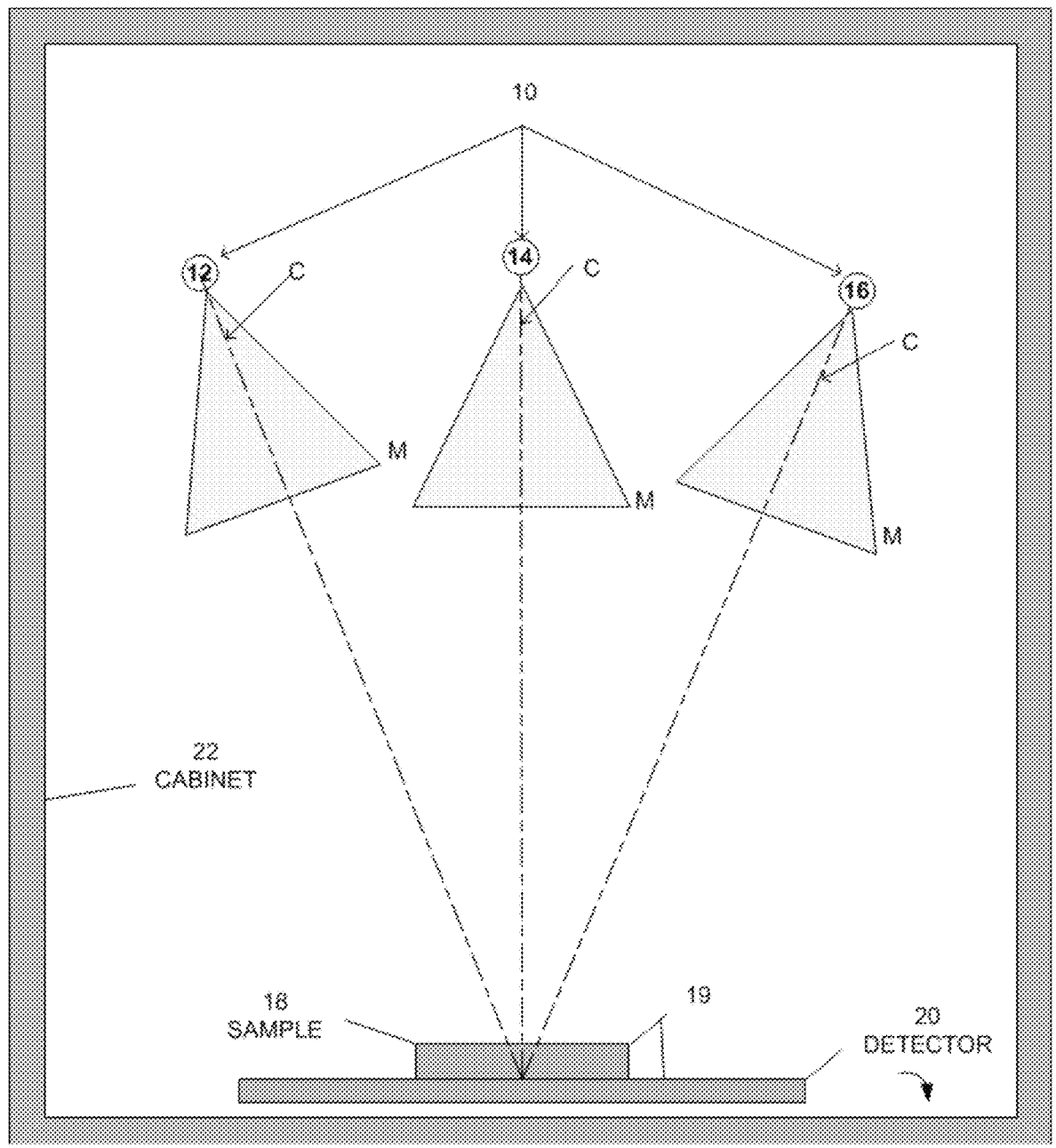
FIG. 1—Schematically illustrates a front view of an X-ray source, a specimen/sample, and a digital detector, where the X-ray source moves relative to the specimen for imaging the specimen at different angles, in one embodiment of a system incorporating aspects of the present disclosure.

One embodiment of a system 100 incorporating aspects of the present disclosure is illustrated in FIG. 1. The system 100 is totally enclosed or housed in an X-ray cabinet 22. In accordance with the aspects of the disclosed embodiments, the X-ray source 10 moves around the stationary sample, 18, typically, but not necessarily, in an arc. References 12, 14, and 16 of FIG. 1 illustrate exemplary positions of the X-ray source 10 within the X-ray cabinet 22. The reference "C" at each of the positions 12, 14, 16 of the X-ray source 10 in FIG. 1 refers to the point source of the X-ray beam. The reference "M" refers to the spread or fan of the X-ray beam.

While the detector 20 may move or rotate, in accordance with one aspect of the present disclosure, the detector 20 remains stationary relative to the sample 18 and X-ray source 10 to maintain an equidistant center point. The X-ray data taken at each of a number of exemplary positions 12, 14, 16 of the X-ray source 10 relative to the sample 18 within the X-ray cabinet 22 is processed to form images, where two or more of the differing image positions are utilized to form a digital tomosynthesis image.

In one embodiment, the aspects of the present disclosure limit the arc or linear travel of the x-ray source 10 over about a 20° to about a 50° arc, preferable about 30°, more preferable 20°. The movement can be clockwise or counter clockwise along a path, which includes for example, one or more, or a combination thereof, of the following exemplary ranges: between approximately 350° (reference position 12) to 0° (reference position 14) to 10° (reference position 16), or between approximately 340° (reference position 12) to 0° (reference position 14) to 20° (reference position 16) and or between approximately 335° (reference position 12) to 0° (reference position 14) to 25° (reference position 16). The ranges recited herein are intended to be approximate and inclusive of start and endpoints. In the example of FIG. 1 the detector 20 is stationary as is the sample 18. The sample 18 also referred to as the "object" or "imaging object" is disposed on or rests on the specimen platform 19 (which is a protective cover) or other surface of the detector 20.

In operation, source 10 is energized to emit an x-ray beam, generally throughout its travel along one or more of the paths or positions described above. The x-ray beam travels through the sample 18 to the detector 16 and the multiple images collected at varying angles are stored and then utilized for the tomosynthesis reconstruction. The X-ray source 10 may range from about 0 kVp to about 90 kVp, preferably a 50 kVp 1000 μa X-ray source.

Different embodiments of the present disclosure can utilize different ranges of motion of one or more of the X-ray source 10 and detector 20 as well as changing the angularity of one or both. The inventive aspects of the present disclosure differ from the prior art in that in prior art systems either the detector and X-ray source 10 and/or the isocenter is above the sample and not at the detector surface. In accordance with the aspects of the present disclosure, in one embodiment, the X-ray source 10 is configured to move, as described herein, while the detector is configured to remain stationary or in a fixed position.

The detector 20 and associated electronics generate image data in digital form for each pixel at each of the angular positions, 12, 14, 16 of X-ray source 10 and translations positions of the detector 20 relative to the sample 18. While only three positions 12, 14, 16 are illustrated in FIG. 1, in practice more images are taken at differing angles. For example, in one embodiment, images can be taken at approximately every 1° of rotation or motion of source 10.

Figure 2:
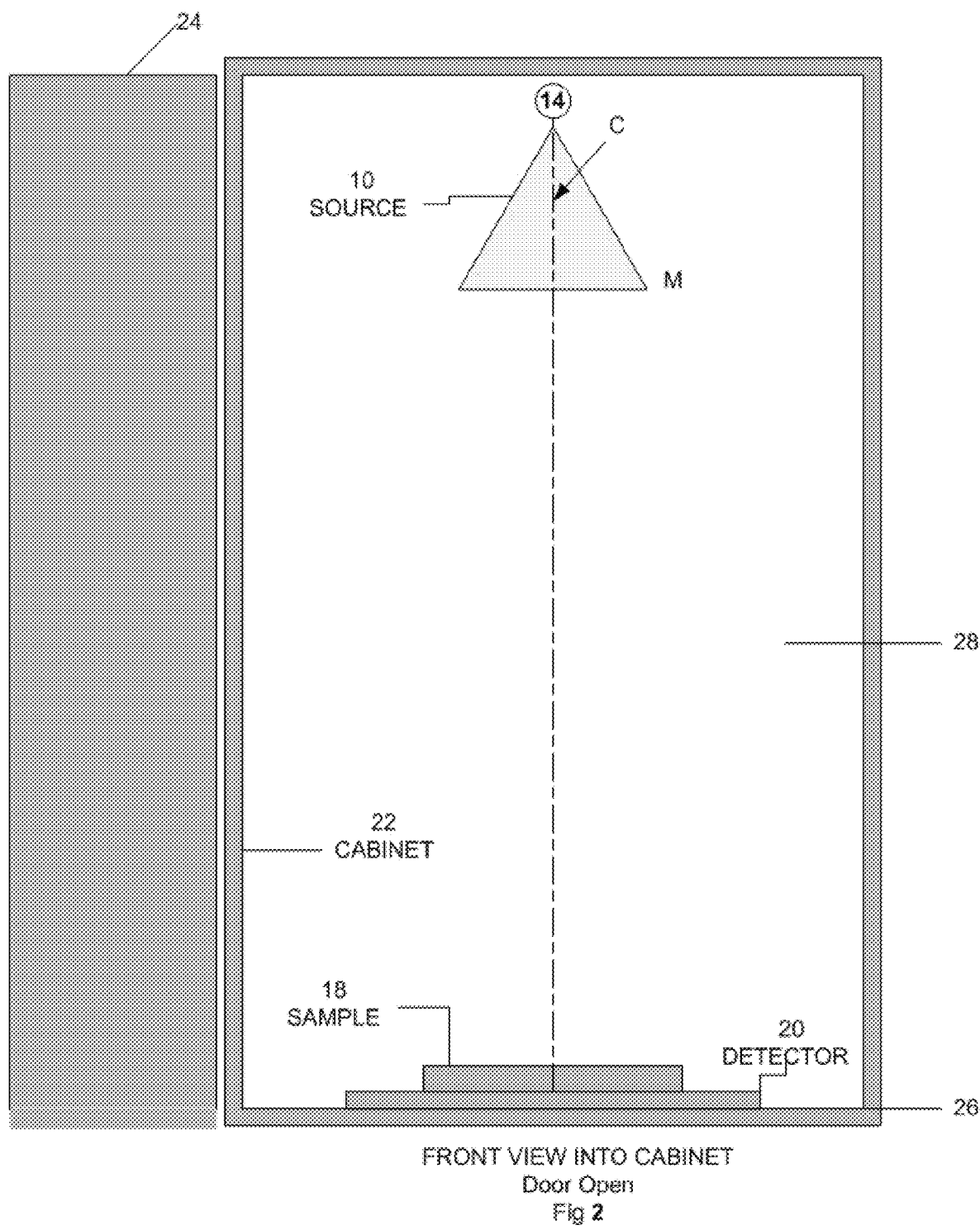
FIG. 2—Schematically illustrates an exemplary orientation of the X-ray source, specimen, and digital detector as viewed when the door of the cabinet is open, in one embodiment of a system incorporating aspects of the present disclosure.

FIG. 2 schematically illustrates one embodiment of the orientation of the X-ray source 10 as seen when the door 24 is opened and the X-ray source 10 is locate at approximately 0°, reference point 14 in this example, within the X-ray cabinet 22. In this embodiment, the motion of the X-ray source 10 can generally occur from the back to the front of the X-ray cabinet 22 with the detector 20 oriented, or otherwise disposed, at the base 26 of the X-ray cabinet 22, within the X-ray cabinet chamber 28. In one embodiment, the detector 20 is suitably coupled to the base 26 of the X-ray cabinet 22. The X-ray spread in this example can be from about 0 kVp to about 50 kVp with the system preferably utilizing an AEC (Automatic Exposure Control) to ascertain the optimal setting to image the object or sample 18 being examined.

In one embodiment, the detector 20, X-ray source 10, and the swing arm 60 (FIG. 5) servo mechanism are controlled via a combination of one or more of software and hardware, such as non-transitory machine-readable instructions stored in a memory that are executable by one or more processors. On example of such a configuration can include controller cards of a computer 470 (FIG. 4), such as a MS Windows based computer. In one embodiment, non-transitory machine-readable instructions being executed by one or more processors of the computer 470 is utilized to compile data received from the detector 20 and present resulting images to a suitable display or monitor 472 (FIG. 4) at each imaging position, such as positions 12, 14 and 16 shown in FIG. 1, the detector 20 generates the respective digital values for the pixels in a two-dimensional array. The size of detector 20 may range, for example, from about 5.08 centimeters by 5.08 centimeters to about 40.64 centimeters by 40.64 centimeters, preferably about 12.7 centimeters by 15.24 centimeters. In one example, detector 20 has a rectangular array of approximately 1536×1944 pixels with a pixel size of 74.8 micrometers. The image dataset attained at each respective position may be processed either at the full spatial resolution of detector 20 or at a lower spatial resolution by overlapping or binning a specified number of pixels in a single combined pixel value.

For example, if we bin at a 2×2 ratio, then there would be an effective spatial resolution of approximately 149.6 micrometers. This binning may be achieved within the original programming of the detector 20 or within the computer 470 providing the tomosynthetic compilation and image.

Figure 3:
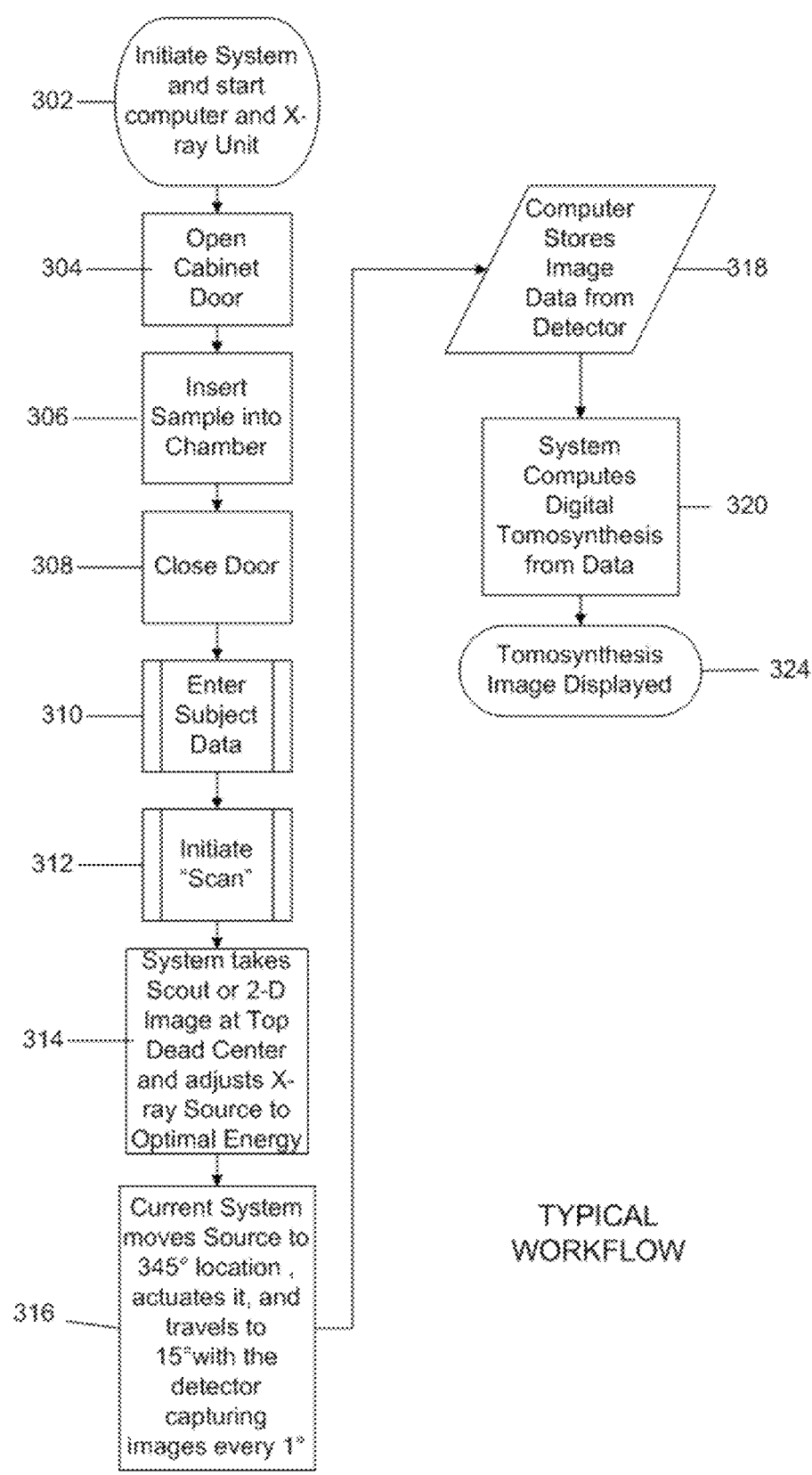
FIG. 3—Displays an exemplary workflow/flowchart of an aspect of the disclosed embodiments.

FIG. 3 illustrates one embodiment of an exemplary workflow from initiating 302 the system 100 through imaging, reconstruction and display 324 of data images collected of the sample 18.

As will be generally understood, the system 100 is initiated 302, the X-ray cabinet door 24 opened 304, and the sample 18 placed into 306 the X-ray cabinet chamber 28. As shown in FIG. 2, for example, the sample 18 is positioned on the detector 20 in a suitable manner. The door 24 is closed 308.

The data and information regarding the sample 18, including any other suitable information or settings relevant to the imaging process and procedure, is entered 310 into the computer 470. The scan is initiated 312. The system 100 will take 314 scout or 2-D images at Top Dead Center, which for purposes of this example is position 14 of FIGS. 1 and 2. The X-ray source 10 can then be moved to other positions, such as positions 12 and 16, and the detector 20 can be used to capture 316 images at various increments along the travel path of the X-ray source 10, such as about every 1 degree.

The captured images are stored 318 and digital tomosynthesis is performed 320. The tomosynthesis image is then displayed 324.

Other embodiments of a system 100 incorporating aspects of the present disclosure are illustrated in FIGS. 1 and 2 where system 100 is totally enclosed or housed in an x-ray cabinet 22 and the x-ray source 10 is stationary relative to the stationary sample, 18 and can be used to obtain a 2-D image. In these embodiments, x-ray source 10 can be positioned at position 14 and the reference "C" refers to the point source of the x-ray beam and the reference "M" refers to the spread or fan of the x-ray beam. While the detector 20 may move or rotate, in accordance with one aspect of the present disclosure, the detector 20 can remain stationary relative to the sample 18 and x-ray source 10 to maintain an equidistant center point. The sample 18 also referred to as the "object" or "imaging object" may be disposed on or rest on the specimen platform 19 (which is a protective cover) or other surface of the detector 20. As with the previous embodiments described herein, the inventive aspects of the present disclosure differ from the prior art in that in prior art systems either the detector and x-ray source 10 and/or the isocenter is above the sample and not at the detector surface. In operation, source 10 is energized to emit an x-ray beam at position 14, located at approximately 0°, and thereby obtain a 2-D image of sample 18. In operation, source 10 is energized to emit an x-ray beam, generally throughout its travel along one or more of the paths or positions described above. The x-ray beam travels through the sample 18 to the detector 16 and to 2-D image is stored. The x-ray source 10 may range from about 0 kVp to about 90 kVp, preferably a 50 kVp 1000 µa x-ray source.

Figure 4:
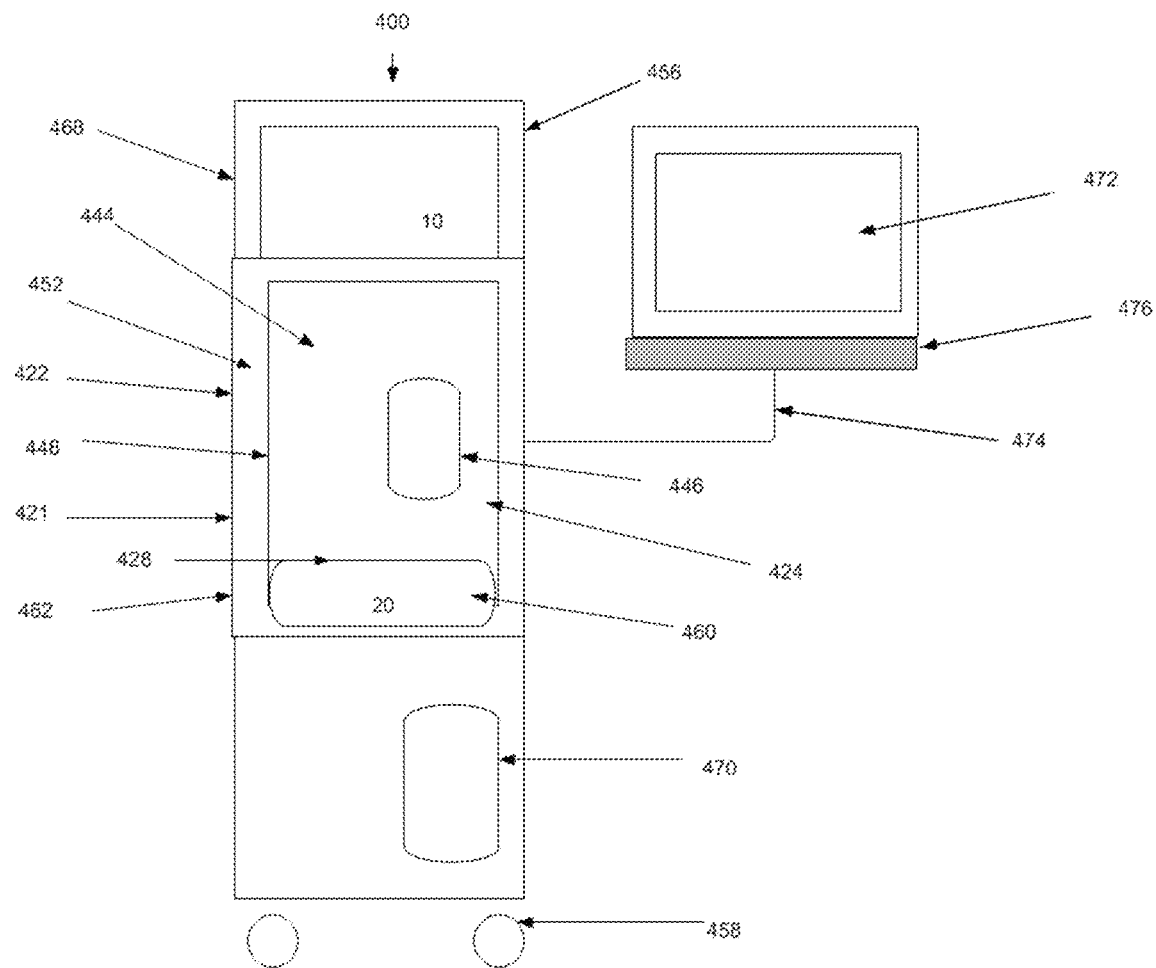
FIG. 4—Displays an example of an X-ray Cabinet System incorporating aspects of the present disclosure.

FIG. 4 shows one embodiment of an X-ray Cabinet System 400 incorporating aspects of the present disclosure. In this embodiment, the X-ray Cabinet System 400 is mounted on wheels 458 to allow easy portability. In alternate embodiments, the X-ray Cabinet System 400 can be mounted on any suitable base or transport mechanism. The cabinet 422 in this example, similar to the exemplary X-ray cabinet 22 of FIG. 1, is constructed of a suitable material such as steel. In one embodiment, the cabinet 422 comprises painted steel defining a walled enclosure with an opening or cabinet chamber 428. Within the cabinet chamber 428, behind door 424, resides an interior space forming a sample chamber 444, which in this example is constructed of stainless steel. Access to the sample chamber 444 is via an opening 446. In one embodiment, the opening 446 of the sample chamber 444 has a suitable door or cover, such as a moveable cover 448. In one embodiment, the moveable cover 448 comprises a door which has a window of leaded glass.

Between the outer wall 421 of cabinet 422 and the sample chamber 444 are sheets of lead 452 that serve as shielding to reduce radiation leakage emitted from the X-ray source 10. In the example of FIG. 4, the X-ray source 10 is located in the upper part 456 of the cabinet 422, in the source enclosure 468. The detector 20 is housed in the detector enclosure 460 at an approximate midpoint 462 of the cabinet 422.

Figure 5:
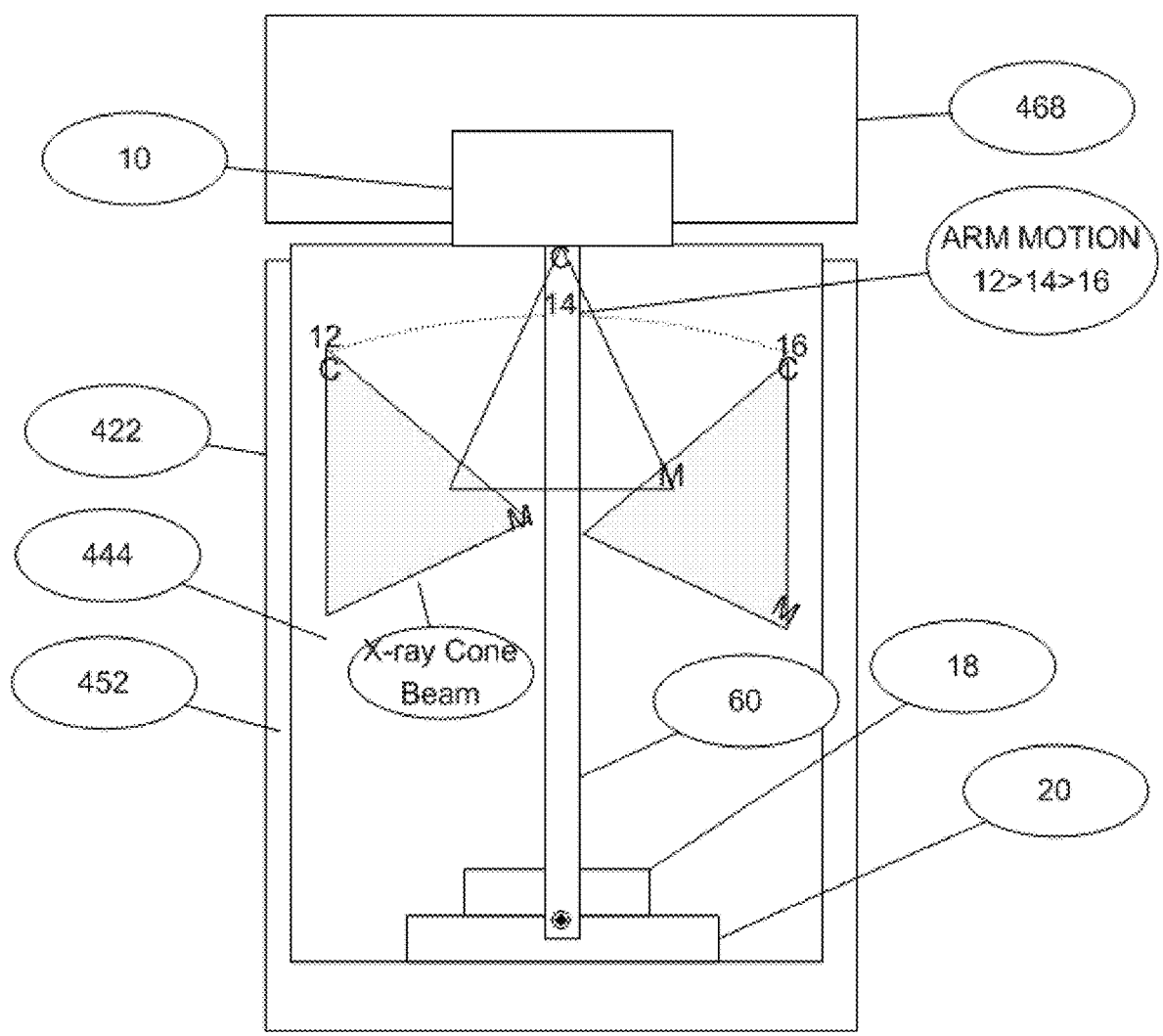
FIG. 5—Displays the sample chamber of the embodiment of FIG. 4 with the swing arm and a detector.
Figure 6:
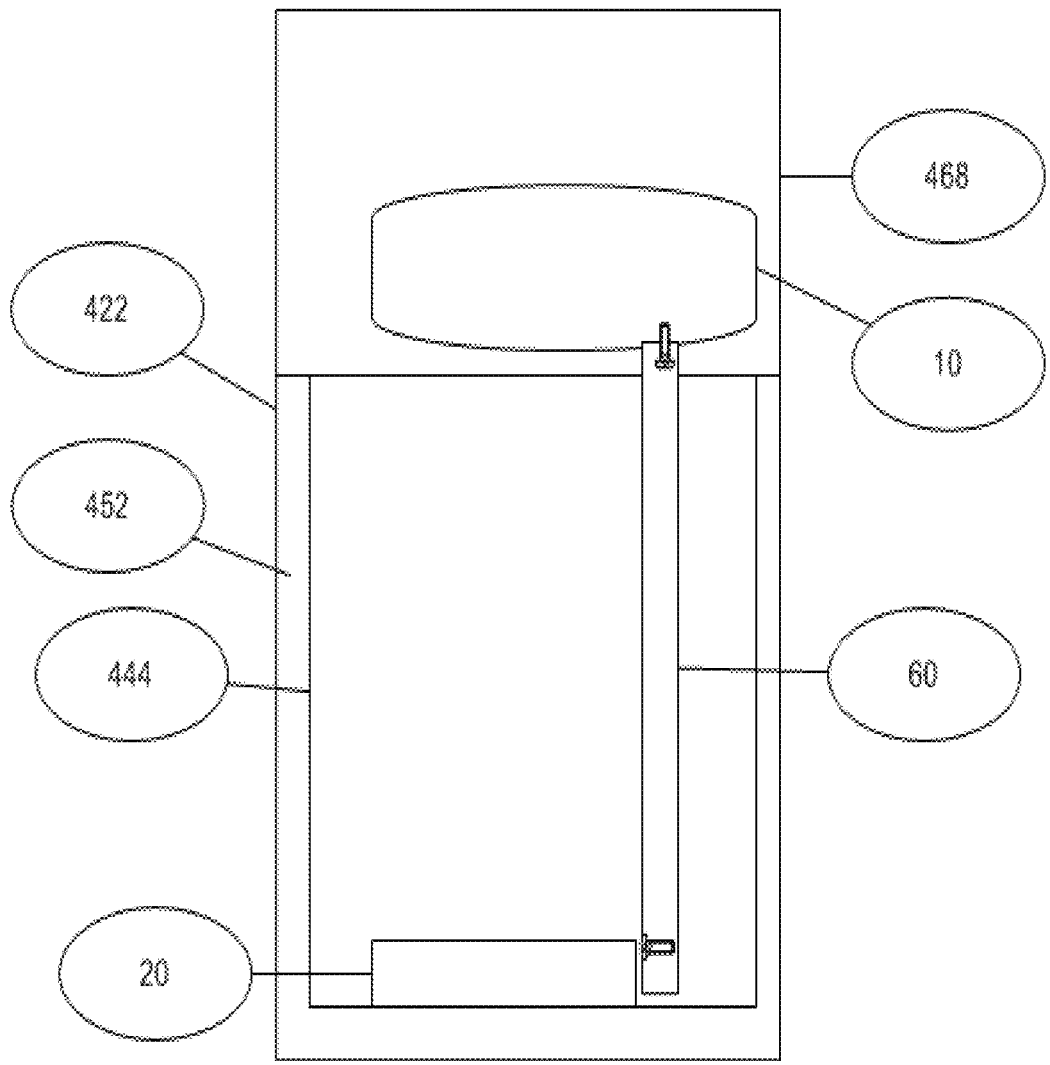
FIG. 6—Displays the lateral view of the X-ray source of the embodiment of FIG. 4 mounted to the top of the swing arm.

In one embodiment, a controller or computer 470 controls the collection of data from the detector 20, controls the swing arm 60 shown in FIGS. 5 & 6, and X-ray source 10. A monitor 472 displays the compiled data and can, for example, be mounted on an articulating arm 474 that is attached to the cabinet 422. The computer 470 receives commands and other input information entered by the operator via a user interface 476, such as a keyboard and/or mouse for example. In one embodiment, the computer 470 can comprise a touch screen or near touch screen device. Although the aspects of the disclosed embodiments will generally be described with respect to a computer 470, it will be understood that the computer 470 can comprise any suitable controller or computing device. Such computing devices can include, but are not limited to, laptop computers, mini computers, tablets and pad devices.

The computer 470 can be configured to communicate with the components of the X-ray cabinet system 400 in any suitable manner, including hardwired and wireless communication. In one embodiment, the computer 470 can be configured to communicate over a network, such as a Local Area Network or the Internet.

FIG. 5 shows a front interior view and FIG. 6 shows a lateral interior view of the sample chamber of imaging unit cabinet of FIG. 4. In this embodiment, a sample 18 is placed or otherwise disposed onto the detector 20. Using the computer 470 shown in FIG. 4, the operator enters in the parameters for the scan via the user interface 476, which can be displayed on the monitor 472. As used herein, the term "display" or "monitor" means any type of device adapted to display information, including without limitation CRTs, LCDs, TFTs, plasma displays, LEDs, and fluorescent devices. The computer 470 then sends the appropriate commands to the X-ray source 10 and detector 20 to activate image collection while the swing arm 60 is moving along a path or arc from position 14 to 12 to 16 (which are shown in FIGS. 1 and 5) or vice versa as described, which in this embodiment are at 345°, 0°, and 15° respectively with 0° at top dead center. At the end of the travel of the swing arm 60 at either position 12 or 16, the computer 470 issues the command to the X-ray source 10 and the detector 20 to cease operating. The individual 2-dimensional (2-D) images which were collected, in this example at 1° increments, are then tabulated in the computer 470 to create the tomosynthetic images. In one embodiment, the operator may select which images they wish via the user interface 476 as they are being displayed on the monitor 472. In one embodiment, the devices and components of the X-ray cabinet system 400 are suitably communicatively coupled together, including one or more of hard wire connections or wireless connections using a suitable wireless connection and communication transmission protocol, as will generally be understood. The X-ray cabinet system 400 can also be configured to transfer images via USB, CD-ROM, or WIFI.

The dynamic imaging software of the disclosed embodiments reconstructs three-dimensional images (tomosynthesis) from two-dimensional projection images in real-time and on-demand. The software offers the ability to examine any slice depth, tilt the reconstruction plane for multiplanar views and gives higher resolution magnifications. FIGS. 7A, 7B, and 7C illustrate exemplary images of an apple using the above process.

FIG. 7A is an image of a slice of the apple at it's very top. 59 mm from the bottom. FIG. 7B is an image of an apple computed at 30.5 mm up from the detector, and FIG. 7C is a view of the apple computed at 13.5 mm from the bottom.

The real-time image reconstruction of the present disclosure enables immediate review, higher throughput, and more efficient interventional procedures reducing patient call backs and data storage needs. Multiplanar reconstruction enables reconstruction to any depth, magnification and plane, giving the viewer the greater ability to view and interrogate image data, thereby reducing the likelihood of missing small structures. Built-in filters allow higher in plane resolution and image quality during magnification for greater diagnostic confidence. Software is optimized for performance using GPU Technology.

The reconstruction software used in conjunction with the aspects of the present disclosure provides the users greater flexibility and improved visibility of the image data. It reconstructs images at any depth specified by the user rather than at fixed slice increments. With fixed slice increments, an object located between two reconstructed slices, such as a calcification, is blurred and can be potentially missed. The aspects of the present disclosure provide for positioning the reconstruction plane so that any object is exactly in focus. This includes objects that are oriented at an angle to the detector 20. The aspects of the present disclosure provide for the reconstruction plane to be angled with respect to the detector plane.

Referring to FIG. 8, an embodiment of a voice-enabled cabinet x-ray unit is shown utilizing the system/cabinet 400 example previously shown in FIG. 4. The medical professional or other authorized operator (e.g., physician, radiologist, surgeon, etc.) can speak a voice command or voice-initiated action that includes proprietary voice-initiated keyword or keywords, preferably proprietary voice-initiated keyword or keywords, into the microphone 805 (e.g. a trigger word and action word or words, such as a verb or verbs), i.e. "Mozart Zoom-in", "Mozart Show K-View", where "Mozart" is the keyword and "Zoom-in" is the verb/action item. The microphone 805 transforms the audible command to an analog signal and sends the analog signal/data created by the microphone 805 via a cable 806 to computer 470 which in turn interprets the voice-initiated keyword or keywords, preferably proprietary voice-initiated keyword or keywords, for example, a trigger word, such as, for example, the machine name (e.g., trademark (including state or country registered trademarks) or tradename), for example "Mozart" or "Xpert" and action word or words which include instructions to performs the requested action, such as, for example, "Zoom-in" and change the image parameters from one image to a different image, the action words may be proprietary as well including commands unique to the x-ray apparatus (e.g., trademark (including state or country registered trademarks) or tradename). This, in turn, provides more flexibility for a clinician or other user of the system to visualize the image data performed previously, provides efficiencies, and simplifies the procedure. Manual input for operation of the cabinet x-ray unit 400 may also be initiated via user interface 476, such as a manual user interface, for example, a keyboard and/or mouse, for example, and the resulting image from the manual-initiated or voice-initiated examination is displayed on the screen 472 and configured in accordance with the given command, be it manual-initiated or voice-initiated. Another embodiment can include microphone 805 connected to computer wirelessly using one or more of a variety of wireless data transfer protocols, including Wireless USB, IEEE 802.x, BLUE TOOTH, WIMAX, etc. It will also be appreciated that microphone 805 as described herein may be employed with a wireless, non-wireless (e.g., wired including, for example, a cable), or even hybrid wireless/cabled communication link between microphone 805 and computer 470.

FIG. 9 illustrates one embodiment of a basic workflow and components of the computing device 470. Manual Input items 474 (e.g., keyboard and/or mouse) and 472 (e.g., touch screen display) are included and the voice-initiated microphone 805 communication device as is previously represented in FIG. 8—805. The medical professional 1002 (e.g., physician, radiologist, surgeon, etc.) speaks a voice command or voice-initiated action into the communication device/microphone 805 that, in turn, is in communication with computer 470 that receives the voice command. Voice recognition software 1008 can interpret the voice command. Voice recognition software 1008 will send a signal to the command generator software 1010 if it can to verify that the voice command includes one or more voice-initiated key words. Upon receipt of the signal from the voice recognition software 1008, the command generator software 1010 will in turn will send an appropriate command consistent with the voice command to the signal generator software 1006. Signal generator software 1006 may to verify that the one or more voice-initiated key words utilizing the voice recognition software 1008 and the command generator software 1010 before actuating the device control software 1046. Signal generator software 1006 can send a signal to the device control software 1046 that can communicate pre-determined/programmed actions to the device 400 consistent with the voice command by accessing a keyword glossary of parameters on the image previously attained by the cabinet x-ray system 400 and displayed 472 and making changes to those parameters consistent with the voice command. i.e. "Mozart Zoom-in", "Mozart Show K-View" to manipulate the the image parameters or data. The voice commands can be displayed on the monitor 472 but need not be because affirmation of the command can be confirmed via an action/manipulation of the GUI/image display. For safety sake, preferably voice commands may not utilized to operate the system 400 other than to manipulate image data visualization, but there may be embodiments that can be included to perform other system operation. Also, preferably and to ensure security of actions all actions use of the appropriate trigger word or words should preface the action word or words to, for example, avoid accidental manipulation of the system by the haphazard use of an action word or words. Note that, for clarity, only selected features of the base unit FIG. 8—400, basic computer FIG. 8—470, and the workflow of the computing device are described herein in detail. Indeed, it is appreciated that the system 400 and its individual components can include additional features and components, though not disclosed herein, while still preserving the principles of the present disclosure. Note also that the base computer 470 can be one of any number devices, including a desktop or laptop computer, etc.

The action word or words and resulting change in image parameters from one to another for the embodiments of the present disclosure can generally include, for example, changing the magnification of the image, switching to a different image, highlighting a section or portion of an image and stringing together a series of images to, for example, show changes in the images over time. Examples of action words and the image parameters they affect can include the following: "Zoom In", "Zoom Out" (which refers to increasing or decreasing the image magnification), "Show K View" (which refers to a composite view, a composite view showing a detailed image of all of the slices synthetically composed to remove any geometric magnification and to highlight anomalies that may or may not be obstructed by another or a density, "Up One" and "Down One" (which refer to stepping through the image slices), "Run Animation" and "Stop Animation" (which refer to scrolling through the image slices automatically), "Show Center View" (which refers to 2-D image view), "Show Slice View" (which refers to displaying the image of a 1 mm slices), "Highlight Image" (which refers to highlighting the k-view image to display calcifications), "Show Numbers" and "Hide Numbers" (which refer to displaying which slices contain the calcifications), "Clear Image" (which refers to reset the image), "Show Optical View" and "Hide Optical View" (which refer to displaying a photo view of the specimen under examination) and Go to slice X (which refers to displaying the image of a particular 1 mm slice).

Thus, while there have been shown and described and pointed out fundamental novel features of the invention as applied to the exemplary embodiments thereof, it will be understood that various omissions and substitutions and changes in the form and details of devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

Aspects of the present disclosure may be embodied in other specific forms without departing from its spirit or essential characteristics. The described embodiments are to be considered in all respects only as illustrative, not restrictive. All changes that come within the meaning and range of equivalency of the claims are to be embraced within their scope.

What is claimed is:

1. A cabinet x-ray system including voice command, the system comprising:
   a cabinet comprising a walled enclosure surrounding an interior chamber, a door configured to cover the interior chamber and a sampling chamber within the interior chamber for containing a specimen;
   a display;
   a microphone;
   an x-ray system in the sampling chamber, the x-ray system including:
     an x-ray source;
     an x-ray detector; and
     a specimen platform configured to have the specimen positioned thereon; and
   a controller configured to:
     selectively energize the x-ray source to emit x-rays through the specimen to the x-ray detector;
     control the x-ray detector to collect a projection x-ray image of the specimen when the x-ray source is energized;
     selectively display an x-ray image on the display from the projection x-ray image, the x-ray image on the display including a first x-ray image having a first set of image parameters;
     receive a voice command from the microphone, the voice command including instructions to change the first x-ray image having the first set of image parameters to a second x-ray image having a second set of image parameters, the second set of image parameters being different from the first set of image parameters; and
     change the x-ray image on the display different from the first x-ray image having the first set of image parameters to the second x-ray image having the second set of image parameters.

2. The cabinet x-ray system including voice command of claim 1, wherein the microphone is connected to the controller.

3. The cabinet x-ray system including voice command of claim 1, wherein the voice command includes at least one action word.

4. The cabinet x-ray system including voice command of claim 3, wherein the voice command further includes at least one trigger word.

5. The cabinet x-ray system including voice command of claim 4, wherein at least one of the at least one trigger word and the at least one action word includes at least one proprietary word.

6. The cabinet x-ray system including voice command of claim 5, wherein the at least one proprietary word includes at least one trademark or at least one tradename.

7. The cabinet x-ray system including voice command of claim 3, wherein the at least one action word includes at least one verb.

8. The cabinet x-ray system including voice command of claim 3, wherein the at least one action word includes zoom in, zoom out, show K view, up one, down one, run animation, stop animation, show center view, show slice view, highlight image, show numbers, hide numbers, clear image, show optical view, hide optical view or go to slice X.

9. The cabinet x-ray system including voice command of claim 1, further including a manual user interface to enter manual-initiated commands to the controller.

10. A cabinet x-ray system including voice command, the system comprising:
    a cabinet defining an interior chamber and an equipment enclosure;
    a display;
    a microphone;
    an x-ray system including:
      an x-ray source positioned in the interior chamber;
      an x-ray detector positioned in the interior chamber;
      a specimen platform positioned in the interior chamber and which is a protective cover of and in physical contact with the x-ray detector; and
      a motion control mechanism positioned in the interior chamber and configured for moving the x-ray source to or along a plurality of positions within the interior chamber relative to the specimen disposed on the specimen platform; and
    a controller positioned in the equipment enclosure and configured to:
      selectively energize the x-ray source to emit x-rays through the specimen to the x-ray detector at selected positions of the x-ray source relative to the specimen such that the isocenter of the emitted x-rays at the selected positions is located at a surface of the x-ray detector;
      control the x-ray detector to collect a projection x-ray images of the specimen when the x-ray source is energized at the selected positions, wherein one of the projection x-ray images is a two-dimensional x-ray image taken at standard imaging angle of approximately 0°;
      create a tomosynthetic x-ray image reconstructed from a collection of projection x-ray images;
      process the collection of the projection x-ray images in the controller into one or more reconstructed tomosynthetic x-ray images representing a volume of the specimen and relating to one or more image planes that are selectively the same or different from that of the two-dimensional x-ray image;
      selectively display an x-ray image on the display, the x-ray image on the display including at least one of the two-dimensional x-ray image and the one or more reconstructed tomosynthetic x-ray images and a first x-ray image having a first set of image parameters;
      receive a voice command from the microphone, the voice command including instructions to change the first x-ray image having the first set of image parameters to a second x-ray image having a second set of image parameters, the second set of image parameters being different from the first set of image parameters; and
      change the x-ray image on the display from the first x-ray image having the first set of image parameters to the second x-ray image having the second set of image parameters.

11. The cabinet x-ray system including voice command of claim 10, wherein the microphone is connected to the controller.

12. The cabinet x-ray system including voice command of claim 10, wherein the voice command includes at least one action word.

13. The cabinet x-ray system including voice command of claim 12, wherein the voice command further includes at least one trigger word.

14. The cabinet x-ray system including voice command of claim 13, wherein at least one of the at least one trigger word and the at least one action word includes at least one proprietary word.

15. The cabinet x-ray system including voice command of claim 14, wherein the at least one proprietary word includes at least one trademark or at least one tradename.

16. The cabinet x-ray system including voice command of claim 12, wherein the at least one action word includes at least one verb.

17. The cabinet x-ray system including voice command of claim 12, wherein the at least one action word includes zoom in, zoom out, show K view, up one, down one, run animation, stop animation, show center view, show slice view, highlight image, show numbers, hide numbers, clear image, show optical view, hide optical view or go to slice X.

18. The cabinet x-ray system including voice command of claim 10, further including a manual user interface to enter manual-initiated commands to the controller.

19. A method for manipulating an x-ray image of a cabinet x-ray system using a voice command of a user, wherein the cabinet x-ray system comprises:
    a cabinet comprising a walled enclosure surrounding an interior chamber, a door configured to cover the interior chamber and a sampling chamber within the interior chamber for containing a specimen;
    a display;
    a microphone;
    an x-ray system in the sampling chamber, the x-ray system including:
        an x-ray source;
        an x-ray detector; and
    a specimen platform configured to have the specimen positioned thereon; and
    controller configured to:
        selectively energize the x-ray source to emit x-rays through the specimen to the x-ray detector;
        control the x-ray detector to collect a projection x-ray image of the specimen when the x-ray source is energized;
        selectively display an x-ray image on the display from the projection x-ray image, the x-ray image on the display including a first x-ray image having a first set of image parameters;
        receive a voice command from the microphone, the voice command including instructions to change the first x-ray image having the first set of image parameters to a second x-ray image having a second set of image parameters, the second set of image parameters being different from the first set of image parameters; and
        change the x-ray image on the display different from the first x-ray image having the first set of image parameters to the second x-ray image having the second set of image parameters,
    wherein the method comprises:
        controlling the x-ray detector to collect an x-ray image of the specimen when the x-ray source is energized;
        selectively displaying the first x-ray image having a first set of image parameters on the display;
        receiving a voice command from the user via the microphone, the voice command including instructions to change the first x-ray image having the first set of image parameters to the x-ray image having a second set of image parameters; and
        changing the first x-ray image having the first set of image parameters on the display to the second x-ray image having the second set of image parameters.

20. The method of claim 19, wherein the voice command includes at least one trigger word and at least one action word.

* * * * *